US006963792B1

(12) United States Patent
Green

(10) Patent No.: US 6,963,792 B1
(45) Date of Patent: Nov. 8, 2005

(54) SURGICAL METHOD

(75) Inventor: Philip S. Green, Redwood City, CA (US)

(73) Assignee: SRI International, Menlo Park, CA (US)

( * ) Notice: Subject to any disclaimer, the term of this patent is extended or adjusted under 35 U.S.C. 154(b) by 244 days.

(21) Appl. No.: 08/709,930

(22) Filed: Sep. 9, 1996

Related U.S. Application Data

(63) Continuation of application No. 07/823,932, filed on Jan. 21, 1992, now abandoned.

(51) Int. Cl.$^7$ ............................ G05B 19/04; A61B 1/04
(52) U.S. Cl. ...................... 700/251; 700/264; 600/117; 600/118; 606/46; 606/139
(58) Field of Search ............................ 348/61, 65, 143, 348/159, 207; 600/101, 109, 117, 118, 102, 600/417, 595; 901/1, 2, 9, 30, 33, 34, 36, 901/15–17; H04N 7/18; 395/82, 83, 86, 395/94, 99, 80, 92; 606/130, 46, 139, 53, 606/49; 414/1, 2; 700/247, 248, 251, 259, 700/264, 245, 257

(56) References Cited

U.S. PATENT DOCUMENTS

| 1,418,184 | A | 5/1922 | Trunick ........................ 279/93 |
| 2,815,697 | A | 12/1957 | Saunders-Singer ............. 88/40 |
| 2,901,258 | A | 8/1959 | Brandafi ....................... 279/97 |
| 3,145,333 | A | 8/1964 | Pardini et al. .............. 318/425 |
| 3,463,329 | A | 8/1969 | Gartner ......................... 214/1 |
| 3,818,125 | A | 6/1974 | Butterfield .................. 178/6.5 |
| 3,921,445 | A | 11/1975 | Hill et al. ................. 73/133 R |
| 3,923,166 | A | 12/1975 | Fletcher et al. ................ 901/2 |
| 3,934,201 | A | 1/1976 | Majefski ...................... 381/14 |
| 4,058,001 | A | 11/1977 | Waxman ....................... 73/620 |
| 4,113,115 | A | 9/1978 | Yoshio .................... 214/1 BB |
| 4,150,326 | A | 4/1979 | Engelberger et al. ....... 318/563 |
| 4,221,997 | A | 9/1980 | Flemming .................... 318/574 |
| 4,260,319 | A | 4/1981 | Motoda et al. ............. 414/591 |
| 4,264,266 | A | 4/1981 | Trechsel ..................... 414/730 |
| 4,349,837 | A | 9/1982 | Hinds .......................... 358/93 |

(Continued)

FOREIGN PATENT DOCUMENTS

CH              482 439            1/1970

(Continued)

OTHER PUBLICATIONS

S. Lavallee, "A New System for Computer Assisted Neurosurgery", IEEE Engineering in Medicine & Biology Society 11th International Conference, pp. 926-927 vol. 3, Nov. 1989.*

(Continued)

*Primary Examiner*—Leo Picard
*Assistant Examiner*—Steven R. Garland
(74) *Attorney, Agent, or Firm*—Townsend&Townsend&CrewLLP; Mark D. Barrish

(57) ABSTRACT

A teleoperator system with telepresence is shown which includes right and left hand controllers (72R and 72L) for control of right and left manipulators (24R and 24L) through use of a servomechanism that includes computer. The teleoperator system comprises a surgical system suited for endoscopic surgery. The surgical system includes a surgical instrument, a servomechanism and a controller. The surgical includes an insertion section and a control section. The insertion section comprises a forearm, a wrist and an end effector in the form of a surgical instrument head selected from the group consisting of retractors, electrosurgical cutters, electrosurgical coagulators, forceps, needle holders, scissors, blades and irrigators. The control section comprises a plurality of motors and linkages which operate to insert and retract the forearm, rotate the forearm, pivot the forearm, and pivot the wrist link about the wrist joint.

9 Claims, 9 Drawing Sheets

U.S. PATENT DOCUMENTS

| | | | |
|---|---|---|---|
| 4,367,998 A | 1/1983 | Causer | 414/4 |
| 4,419,041 A | 12/1983 | Rose | 414/739 |
| 4,436,684 A | 3/1984 | White | 264/138 |
| 4,456,961 A | 6/1984 | Price et al. | 364/513 |
| 4,474,174 A | 10/1984 | Petruzzi | 128/4 |
| 4,490,022 A | 12/1984 | Reynolds | 351/211 |
| 4,503,854 A | 3/1985 | Jako | 128/303.1 |
| 4,506,393 A | 3/1985 | Murphy | 3/1 |
| 4,510,574 A | 4/1985 | Guittet et al. | 901/2 |
| 4,517,963 A | 5/1985 | Michel | 128/6 |
| 4,562,463 A | 12/1985 | Lipton | 358/88 |
| 4,582,067 A | 4/1986 | Silberstein | 128/663 |
| 4,583,117 A | 4/1986 | Lipton et al. | 358/92 |
| 4,601,000 A | 7/1986 | Montabert | 364/513 |
| 4,636,138 A | 1/1987 | Gorman | 414/735 |
| 4,638,799 A | 1/1987 | Moore | 128/303 B |
| 4,651,201 A | 3/1987 | Schoolman | 358/98 |
| 4,672,963 A | 6/1987 | Barken | 128/303.1 |
| 4,722,056 A | 1/1988 | Roberts et al. | 364/413 |
| 4,728,974 A | 3/1988 | Nio et al. | 354/81 |
| 4,744,363 A | 5/1988 | Hasson | 128/321 |
| 4,750,475 A | 6/1988 | Yoshihashi | 128/6 |
| 4,751,925 A | 6/1988 | Tontarra | 128/303 R |
| 4,762,455 A | 8/1988 | Coughlan et al. | 414/4 |
| 4,764,944 A | 8/1988 | Finlayson | 378/20 |
| 4,788,482 A | 11/1988 | Tachibana et al. | 318/616 |
| 4,791,588 A | 12/1988 | Onda et al. | 364/513 |
| 4,791,934 A | 12/1988 | Brunnett | 128/653 |
| 4,806,066 A | 2/1989 | Rhodes et al. | 414/729 |
| 4,808,898 A | 2/1989 | Pearson | 318/568 |
| 4,815,006 A | 3/1989 | Andersson et al. | 364/513 |
| 4,826,392 A | 5/1989 | Hayati | 414/730 |
| 4,833,383 A | 5/1989 | Skarr et al. | 318/568.16 |
| 4,837,703 A | 6/1989 | Kakazu et al. | 364/474.18 |
| 4,837,734 A | 6/1989 | Ichikawa et al. | 901/2 |
| 4,853,874 A | 8/1989 | Iwamoto et al. | 364/513 |
| 4,854,301 A | 8/1989 | Nakajima | 128/4 |
| 4,855,822 A | 8/1989 | Narendar et al. | 358/103 |
| 4,860,215 A | 8/1989 | Seraji | 364/513 |
| 4,862,873 A | 9/1989 | Yajima et al. | 128/6 |
| 4,863,133 A | 9/1989 | Bonnell | 248/278 |
| 4,873,572 A | 10/1989 | Miyazaki et al. | 358/98 |
| 4,899,730 A | 2/1990 | Stennert et al. | 128/4 |
| 4,921,393 A | 5/1990 | Andeen et al. | 414/729 |
| 4,922,338 A | 5/1990 | Arpino | 358/93 |
| 4,930,494 A | 6/1990 | Takehana et al. | 128/4 |
| 4,941,106 A | 7/1990 | Krieger | 364/513 |
| 4,942,539 A | 7/1990 | McGee et al. | 364/513 |
| 4,943,296 A | 7/1990 | Funakubo et al. | 606/166 |
| 4,947,702 A | 8/1990 | Kato | 74/479 |
| 4,979,949 A * | 12/1990 | Matsen, III et al. | 606/53 |
| 4,989,253 A | 1/1991 | Liang et al. | 381/110 |
| 4,996,975 A | 3/1991 | Nakamura | 128/6 |
| 5,002,418 A | 3/1991 | McCown et al. | 403/24 |
| 5,020,001 A | 5/1991 | Yamamoto et al. | 364/513 |
| 5,020,933 A | 6/1991 | Salvestro et al. | 403/90 |
| 5,036,463 A | 7/1991 | Abela et al. | 364/413.13 |
| 5,045,936 A | 9/1991 | Lobb et al. | 358/98 |
| 5,046,022 A | 9/1991 | Conway et al. | 364/513 |
| 5,050,608 A | 9/1991 | Watanabe et al. | 128/653 R |
| 5,060,532 A | 10/1991 | Barker | 74/479 |
| 5,062,761 A | 11/1991 | Glachet | 414/729 |
| 5,077,506 A | 12/1991 | Krause | 318/71 |
| 5,078,140 A | 1/1992 | Kwoh | 128/653.1 |
| 5,078,142 A | 1/1992 | Siczek et al. | 128/653.1 |
| 5,086,401 A * | 2/1992 | Glassman et al. | 395/94 |
| 5,090,401 A | 2/1992 | Schwieker | 128/24 EL |
| 5,096,236 A | 3/1992 | Thony | 292/32 |
| 5,097,839 A | 3/1992 | Allen | 128/653.1 |
| 5,098,426 A | 3/1992 | Sklar et al. | 606/5 |
| 5,125,888 A | 6/1992 | Howard et al. | 600/12 |
| 5,141,519 A | 8/1992 | Smith et al. | 606/205 |
| 5,142,930 A | 9/1992 | Allen et al. | 74/469 |
| 5,154,717 A | 10/1992 | Matsen, III et al. | 606/53 |
| 5,170,347 A | 12/1992 | Tuy et al. | 364/413.22 |
| 5,182,641 A | 1/1993 | Diner et al. | 358/103 |
| 5,184,601 A * | 2/1993 | Putman | 600/102 |
| 5,187,574 A | 2/1993 | Kosemura et al. | 358/108 |
| 5,188,111 A | 2/1993 | Yates et al. | 128/657 |
| 5,201,325 A | 4/1993 | McEwen et al. | 428/779 |
| 5,209,747 A | 5/1993 | Knoepfler | 606/16 |
| 5,216,596 A | 6/1993 | Weinstein | 364/413.02 |
| 5,217,003 A * | 6/1993 | Wilk | 600/109 |
| 5,219,351 A | 6/1993 | Teubner et al. | 606/130 |
| 5,221,283 A | 6/1993 | Chang | 606/130 |
| 5,222,499 A | 6/1993 | Allen et al. | 128/653.1 |
| 5,228,429 A | 7/1993 | Hatano | 128/4 |
| 5,230,338 A | 7/1993 | Allen et al. | 128/653 |
| 5,236,432 A | 8/1993 | Matsen, III et al. | 606/88 |
| 5,240,011 A | 8/1993 | Assa | 128/751 |
| 5,251,127 A | 10/1993 | Raab | 364/413.13 |
| 5,253,706 A | 10/1993 | Reid | 166/135 |
| 5,257,203 A | 10/1993 | Riley et al. | 364/474.05 |
| 5,257,998 A | 11/1993 | Ota et al. | 606/130 |
| 5,260,319 A | 11/1993 | Effland et al. | 514/326 |
| 5,261,404 A | 11/1993 | Mick et al. | 128/653.1 |
| 5,264,266 A | 11/1993 | Yokoyama et al. | 428/64 |
| 5,271,384 A | 12/1993 | McEwen et al. | 128/20 |
| 5,273,039 A | 12/1993 | Fujiwara et al. | 128/653.1 |
| 5,279,309 A | 1/1994 | Taylor et al. | 128/782 |
| 5,280,427 A | 1/1994 | Magnusson et al. | 364/413.01 |
| 5,281,220 A | 1/1994 | Blake, III | 606/46 |
| 5,284,130 A | 2/1994 | Ratliff | 128/20 |
| 5,289,273 A | 2/1994 | Lang | 348/121 |
| 5,299,288 A | 3/1994 | Glassman et al. | 395/80 |
| 5,313,306 A | 5/1994 | Kuban et al. | 348/65 |
| 5,325,866 A | 7/1994 | Krzyzanowski | 128/751 |
| 5,339,799 A | 8/1994 | Kami et al. | 128/4 |
| 5,343,391 A | 8/1994 | Mushabac | 364/413.28 |
| 5,368,015 A | 11/1994 | Wilk | 128/4 |
| 5,368,428 A | 11/1994 | Hussey et al. | 414/1 |
| 5,371,536 A | 12/1994 | Yamaguchi | 348/169 |
| 5,377,310 A | 12/1994 | Jain et al. | 395/95 |
| 5,377,683 A | 1/1995 | Barken | 128/660.03 |
| 5,382,885 A | 1/1995 | Salcudean et al. | 318/568.11 |
| 5,397,323 A | 3/1995 | Taylor et al. | 606/130 |
| 5,398,685 A | 3/1995 | Wilk et al. | 128/653.1 |
| 5,417,210 A | 5/1995 | Funda et al. | 129/653.1 |
| 5,425,528 A | 6/1995 | Rains et al. | 251/149.1 |
| 5,441,505 A | 8/1995 | Nakamura | 606/130 |
| 5,445,166 A | 8/1995 | Taylor | 128/897 |
| 5,474,566 A | 12/1995 | Alesi et al. | 606/139 |
| 5,480,409 A | 1/1996 | Riza | 606/205 |
| 5,515,478 A | 5/1996 | Wang | 395/86 |
| 5,524,180 A * | 6/1996 | Wang et al. | 600/118 |
| 5,553,198 A | 9/1996 | Wang et al. | 395/80 |
| 5,571,110 A | 11/1996 | Matsen, III et al. | 606/88 |
| 5,572,999 A | 11/1996 | Funda et al. | 128/653.1 |
| 5,630,431 A | 5/1997 | Taylor | 128/697 |
| 5,636,138 A | 6/1997 | Gilbert et al. | 364/512 |
| 5,762,458 A * | 6/1998 | Wang et al. | 414/1 |
| 5,815,640 A * | 9/1998 | Wang et al. | 395/86 |
| 5,841,950 A * | 11/1998 | Wang et al. | 395/99 |
| 5,855,583 A * | 1/1999 | Wang et al. | 606/139 |
| 5,878,193 A * | 3/1999 | Wang et al. | 395/86 |
| 5,907,664 A * | 5/1999 | Wang et al. | 395/86 |

FOREIGN PATENT DOCUMENTS

| | | |
|---|---|---|
| DE | 28 19 976 | 5/1978 |
| DE | 3806190 | 9/1988 |
| DE | 4 213 426 | 10/1992 |
| EP | 0 239 409 A1 | 3/1987 |
| EP | 02 39 409 | 9/1987 |

| | | |
|---|---|---|
| EP | 0 291 292 A2 | 5/1988 |
| EP | 0 595 291 A1 | 10/1993 |
| EP | 0776 738 A2 | 6/1997 |
| FR | 2 460 762 | 1/1979 |
| FR | 86 00852 | 1/1986 |
| FR | 2 593 106 | 7/1987 ............ B25J 11/00 |
| GB | 2040134 | 8/1980 |
| GB | 2117732 | 10/1983 |
| JP | 59-146770 A | 8/1984 |
| JP | 62-29196 B2 | 6/1987 |
| JP | 2-15349 B2 | 4/1990 |
| WO | WO 91/04711 | 4/1991 |
| WO | WO 92/16141 | 10/1992 |
| WO | WO 93/13916 | 7/1993 |
| WO | WO 94/03113 | 2/1994 |
| WO | WO 94/18881 | 9/1994 |
| WO | WO 94/26167 | 11/1994 |
| WO | WO 95/01757 | 1/1995 |

OTHER PUBLICATIONS

B. Preising et al, "A Literature Review: Robots in Medicine IEEE Engineering in Medicine" IEEE Engineering in Medicine and Biology Magazine vol. 10, Issue 2, pp. 13-22, 71, Jun. 1991.*

A.M. Sabatini et al. "Force Feedback-Based Telemicromanipulation for Robot Surgery on Soft Tissues" IEEE Engineering in Medicine & Biology Society 11th Annual International Conference pp. 890-891, vol. 3, Nov. 1989.*

Bergamasco et al. "Advanced Interfaces for Teleoperated Biomedical Robots" IEEE Engineering in Medicine & Biology Society 11th Annual International Conference pp. 912-913, vol. 3, Nov. 1989.*

Asada Haruhiko et al., "Development of a Direct-Drive Arm Using Arm Using High Torque Brushless Motors," Chapter 7, pp. 583-599.

Guerrouad Aicha et al., "S.M.O.S.: Stereotaxical Microtelemanipulator for Ocular Surgery," *IEEE Engineering in Medicine & Biology Society*, 11th Annual International Conference, 1989, Medical Applications of Robotics, Track 16: Biorobotics, pp. 879-880.

Kazerooni H., "Design and Analysis of the Statically Balanced Direct-Drive Robot Manipulator," *Robotics & Computer-Integrated Manufacturing*, 1989, vol. 6, No. 4, pp. 287-293.

Ng. W. S. et al., "Robotic Surgery," *IEEE Engineering in Medicine and Biology*, Mar. 1993, pp. 120-125.

Taubes Gary, "Surgery in Cyberspace," *Discover*, Dec. 1994, pp. 85-92.

Taylor Russell H. et al., "A Telerobotic Assistant for Laparoscopic Surgery," *Engineering in Medicine and Biology*, May-Jun. 1995, pp. 279-288.

Trevelyan James P. et al., "Motion Control for a Sheep Shearing Robot," *IEEE Robotics Research Conference*, the 1st International Symposium, Carroll, NH, USA, Conference Date: Aug. 25, 1983, Conference No. 05357, Publication by MIT Press, pp. 175-190.

A.D. Alexander, III, "Impacts of Telemation on Modern Society", *, *1st CISM-IFTO MM Symposium*, vol. 2, pp. 122-136.

A.K. Bejczy et al, "Controlling Remote Manipulators Through Kinesthetic Coupling", 1983, *Computers in Mechanical Engineering*, pp. 48-60.

Fisher et al., "Virtual Interface Environment", 1986, *Proceedings IEEE/IAAA 7th Digital Avionics Systems Conference*, pp. 346-350.

Hald et al., "Telepresence, Time Delay and Adaptation", *, *Spatial Displays and Spatial Instruments Proceedings of a Conference sponsored by NASA Ames Research Center and the School of Optometry, Univ. of California*, pp. 28-1 through 28-16.

Kim et al., "A Helmet Mounted Display for Telerobotics", 1988, *33 IEEE Computer Society International Conference, California*, pp. 543-547.

B. M. Jau, "Anthropomorphic Remoter Manipulator", 1991, *NASA Tech Briefs*, p. 92.

K. Matsushima, "Servo Micro Manipulator Tiny Micro Mark-1", 1991, *NASA Tech Briefs*, p. 92.

K. Matsushima, "Servo Micro Manipulator Tiny Micro Mark-1", 1982, *4th Symposium on Theory and Practice of Robots and Manipulators*, pp. 193-201.

R. Richter, "Telesurgery may Bridge Future Gaps", 1988, *Times Tribune*, Sunday, Jan. 24, pp. A-1 and A-16.

E. H. Spain, "Stereo Advantage for a Peg-in-Hole Task Using Force-Feedback Manipulator", 1990, *Stereoscopic Displays and Applications*, pp. 244-254.

Tachi et al., "Tele-existence Master Slave System for Remote Manipulation", 1990, *Proceedings of the 29th Conference on Decision and Control*, vol. 1 of 6, pp. 85-90.

"Introduction t a New Project for The National Research Development Program (Large-Scale Project) in FY 1991—Micromachine Technology", 1991, *Agency of Industrial Science and Technology Ministry of International Trade and Industry, Japan*, pp. 1-11.

"Another Pair of Hands for Surgeon?" 1972, *The Blue Cross magazine Perspective*, p. 27.

Bergamasco et al., "Advanced interfaces for teleoperated biomedical robots" *IEEE Engineering in Medicine and Biology Society $11^{th}$ Annual International Conference*, (1989) pp. 0912-0913.

Besant et al., "Camera control for laparoscopic surgery by speech-recognizing robot: Constant attention and better use of personnel" $3^{rd}$ *World Congress of Endoscopic Surgery*, (Jun. 1992) Session CL25/1-5 and Session 15/1-5.

Bowersox et al., "Vascular applications of telepresence surgery: Initial feasibility studies in swine" *Journal of Vascular Surgery* (1996) vol. 23, No. 2, pp. 281-287.

Charles, "Design of a surgeon-machine interface for teleoperated microsurgery" *IEEE IEEE Engineering in Medicine and Biology Society $11^{th}$ Annual International Conference*, (1989) pp. 0883-0884.

Colgate, "Power and impedance scaling in bilateral manipulation" *Proceedings of 1991 IEEE International Conference on Robotics and Automation* (Apr. 1991) pp. 2292-2297.

Corcoran, "Robots for the operating room," *The New York Times, Sunday* (Jul. 1992) 4 pages total.

Das et al., "Kinematic control and visual display of redundant teleoperators," *IEEE* (1989) pp. 1072-1077.

Davies et al., "A surgeon robot for prostatectomies" *IEEE* (1991) pp. 870-877.

Dolan et al., "A robot in an operating room: A bull in a china shop?" *IEEE* (1987) pp. 1096-1097.

Finlay et al., "Controlling the movement of a surgical laparoscope" *IEEE* (May/Jun. 1995) pp. 289-291.

Finlay et al., "Results of a feasibility study into applications for advanced medical robots," *National Research Council Canada/Joint Coordinating Forum for the International Advanced Robotics Programme* (1988) pp. 2.1-2.6.

Flatau, "Compact servo master-slave manipulator with optimized communication links" *Proceedings of 17th conference on remote systems technology* (Nov. 1969) pp. 154-164.

Funda et al., "Constrained Cartesian motion control for teleoperated surgical robots" *IEEE* (1996) vol. 12, No. 3, pp. 453-465.

Gayed et al., "An advanced control micromanipulator for surgical applications" *Systems Science* (1987) vol. 13, No. 1-2, pp. 123-134.

Glauser et al., "Conception of a robot dedicated to neurosurgical operations" *IEEE* (1991) pp. 898-907.

Green et al., "Telepresence Surgery" *IEEE Engineering in Medicine and Biology* (May/Jun. 1995) pp. 324-329.

Guinot et al., "Analysis of a robot wrist device for mechanical decoupling of end-effector position and orientation" *Six CISM-IFToMM symposium on theory and practice of robots and manipulators* (Sep. 1986) pp. 42-53.

Hill et al., "Telepresence surgery demonstration system" *IEEE* (1994) pp. 2302-2307.

Holler et al., "An ATM-based local communication system for telesurgery" *Interactive technology and the new paradigm for healthcare* (1995) pp. 137-146.

Hunter et al., "Manipulation and dynamic mechanical testing of microscopic objects using a tele-micro-robot system" *IEEE Control Systems Magazine* (Feb. 1990) vol. 10, No. 2, pp. 3-9.

Inoue et al., "Six-axis bilateral control of an articulated slave manipulator using a Cartesian master manipulator" *Advanced Robotics*, (1990) vol. 4, No. 2, pp. 139-150.

Kavoussi et al., "Telerobotic assisted laparoscopic surgery: Initial laboratory and clinical experience" *Urology* (Jul. 1994) vol. 44, No. 1, pp. 15-19.

Kazerooni, "Human/robot interaction via the transfer of power and information signals/ Part I: Dynamics and control analysis" *IEEE* (1989) pp. 1632-1640.

Kazerooni, "Human/robot interaction via the transfer of power and information signals/ Part II: An experimental analysis" *IEEE* (1989) pp. 1641-1647.

Kazerooni et al., " The dynamics and control of a haptic interface device" *IEEE Transactions on Robotics and Automation* (Aug. 1994) vol. 10, No. 4, pp. 453-464.

Majima et al., "On a micro-manipulator for medical application-stability consideration of its bilateral controller" *Mechatronics* (1991) vol. 1, No. 3, pp. 293-309.

Soto et al., "The safety assessment of human-robot systems (Architectonic principles of hazard-control systems)," *JSME International Journal* (Mar. 1989) vol. 32, No. 1, pp. 67-74.

Taylor et al., " A telerobotic assistant for laparoscopic surgery," *Computer Science* (Feb. 1994) pp. 1-24.

Taylor et al., "Taming the bull: Safety in a precise surgical robot" *IEEE (1991) pp. 865-873*.

Tejima et al., "A new microsurgical robot system for corneal transplantation" *Precision Machinery* (1988) vol. 2, pp. 1-9.

Tendick et al., "Analysis of the surgeon's grasp for telerobotic surgical manipulation" *IEEE Engineering in Machine and Biology Society 11th Annual International Conference* (1989) pp. 0914-0915.

Thring, "Robots and telechirs: Manipulators with memory; remote manipulators; machine limbs for the handicapped" *Ellis Horwood Series in Engineering Science*, pp. 9-11, Chapter 5: pp. 122-131, Chapter 7: pp. 194-195, Chapter 8: pp. 236-278, Chapter 9: p. 279, 1983.

Trevelyan, "Skills for a shearing robot: Dexterity and sensing" *Robotics Research/Second International Symposium* (1985) pp. 272-282.

Trivedi et al., "Developing telerobotics systems using virtual reality concepts" *IEEE* (Jul. 1993) pp. 352-359.

Vibet, "Properties of master-slave robots," *Motor-Con* (Apr. 1987) pp. 309-316.

VIDEOTAPE: "Telepresence: Advanced Teleoperator Technology for Enhanced Minimally Invasive Surgery," Phil Green (Apr. 1992).

Abstracts and Video Catalogue, 3rd World Congress of Endoscopic Surgery (Jun. 1992); p. 49 an Abstract No. 704.

Askew, et al., "Ground Control Testbed for Space Station Freedom Robot Manipulators", Proceedings of the IEEE Virtual Reality Annual International Symposium, Seattle, Washington, USA, (Sep. 18-22, 1993), *Institute of Electrical and Electronics Engineers*, pp. 69-75.

Galloway, Jr., et al., "A New Device for Interactive, Image-guided Surgery", Proceedings of SPIE Conference on Medical Imaging (Feb. 24-26, 1991), pp. 9-18.

Hayati, et al., "Remote Surface Inspection System", *Robotics and Autonomous Systems*, (1993) Elsevier Science Publs. 11:1:45-59.

Hurteau, et al., "Laparoscopic Surgery Assisted by a Robotic Cameraman: Concept and Experimental Results", Proceedings of IEEE Int'l. Conference on Robotics and Automation, San Diego, California, USA, (May 8-13, 1994) pp. 2286-2289.

Preising, et al., "A Literature Review: Robots in Medicine", *IEEE Engg. in Med. and Bio.* (Jun. 1991) pp. 13-22.

Bowersox, et al., "Vascular Applications of Telepresence Surgery: Initial Feasibility Studies in Swine", *Jour. of Vasc. Surg.*, 23:2 (Feb. 1996), pp. 281-287.

"Intuitive Surgical Sees The Future of Minimally Invasive Surgery," Panasonic Industrial/Medical Group, 1999.

"Medicine Meets Virtual Reality: Discovering Applications for 3-D Multi-Media Interactive Technology in the Health Sciences," Medicine Meets VR, San Diego, CA, Jun. 4-7, 1992.

"The da Vinci™ Endoscopic Instrument Control System User Manual," Intuitive Surgical, Inc., 1999.

Altamuro, V.M., "Automatic Guided Vehicles and Robots," Mark's Standard Handbook for Mechanical Engineers, Ninth Edition, McGraw-Hill Book Company, New York, 1987.

Bose et al., "Tremor Compensation for Robotics Assisted Microsurgery," Proc. Ann. Int'l Conf. IEEE Engineering in Medicine and Bioligy Society, 14(3):1067-1068 (Oct. 1992).

Clement et al., "An Overview of CAT [Computer Assisted Telemanipulator] Control in Nuclear Services," 1985 IEEE Conference on Robotics and Automation, pp. 713-717.

Definition of "attach", Random House Webster's College Dictionary, Random House, Inc., New York, 1997.

Definition of "coupled", Webster's College Dictionary, Random House, Inc., New York, 1991.

Definition of "coupler", Webster's College Dictionary, Random House, Inc., New York, 1991.

Definition of "establish", "original" and "position", Webster's College Dictionary, Random House, Inc., New York, 1991.

Definition of "gimbals", Webster's College Dictionary, Random House Inc., New York, 1994.

Definition of "instrument", Stedman's Medical Dictionary, 26th Edition, Williams & Wilkins, Baltimore, 1995.

Definition of "instrument", Webster's College Dictionary, Random House, Inc., New York, 1991.

Definition of "proportional", Random House Webster's College Dictionary, Random House, Inc., New York, 1997.

Definition of "surgical", Webster's College Dictionary, Random House, Inc., New York, 1991.

Fisher, S.S., "Telepresence Master Glove Controller for Dexterous Robotic End-Effectors," SPIE, vol. 726, Intelligent Robots and Computer Vision: Fifth in a Series, pp. 396-401, 1986.

Fu et al., "Robotics: Control, Sensing, Vision and Intelligence," McGraw-Hill Book Company, 1987, contents pp. vii, viii, ix.

Hannaford et al., "Performance Evluation of Six-Axis Generalized Force-Reflecting Teleoperator" 21/3 IEEE Transactions on Systems, Man and Cybernetics, vol. 21, No. 3 (May/Jun. 1991) at 621, col. 2.

Heer, ed., *Remotely Manned Systems: Exploration and Operation in Space*, Proceedings of the First National Conference, California Institute of Technology, Pasadena, CA, Sep. 13-15, 1972.

http://www.computermotion.com/pressr114.html, News Release "Computer Motion Receives Additional Broad-Based Medical Robotics Patent," Jun. 2, 2000.

Hunter et al., "Opthalmic Microsurgical Robot and Associated Virtual Environment," Computer Biol. Med. 125(2): 173-182 (1995).

Krishnan et al., "Design considerations of a new generation endoscope using robotics and computer vision technology" Abstract No. 276, Session CL 25/2, 1 page, Jun. 1992.

Mair, "Industrial robotics" Prentice Hall Publishers, New York, pp. 41-54, 203-209.

Ogata, K., *Modern Control Engineering*, 2nd Edition, selected pp. 1-4, and 8-9, Prentice Hall, Englewood Cliffs, New Jersey, 1990.

Taylor et al., "A Telerobotic Assistant for Laparoscopic Surgery," Engineering in Medicine and Biology, May-Jun. 1995, pp. 279-288.

Thring, M.W., *Robots and Telechirs: Manipulators with Memory; Remote Manipulators; Machine Limbs for the Handicapped*, Ellis Horwood Limited, Chichester, 1983.

Vertut et al., "Sensor aided and/or computer-aided bilateral teloperation system (SCATS)," Fifth CISM-IFToMM Symposium, Theory and Practice of Robots and Manipulators, Proceedings of RoManSy '84. part 4, MIT Press, Cambridge, Massachusetts, 1985.

US 5,100,411, 03/1992, Koutrouvelis (withdrawn)

* cited by examiner

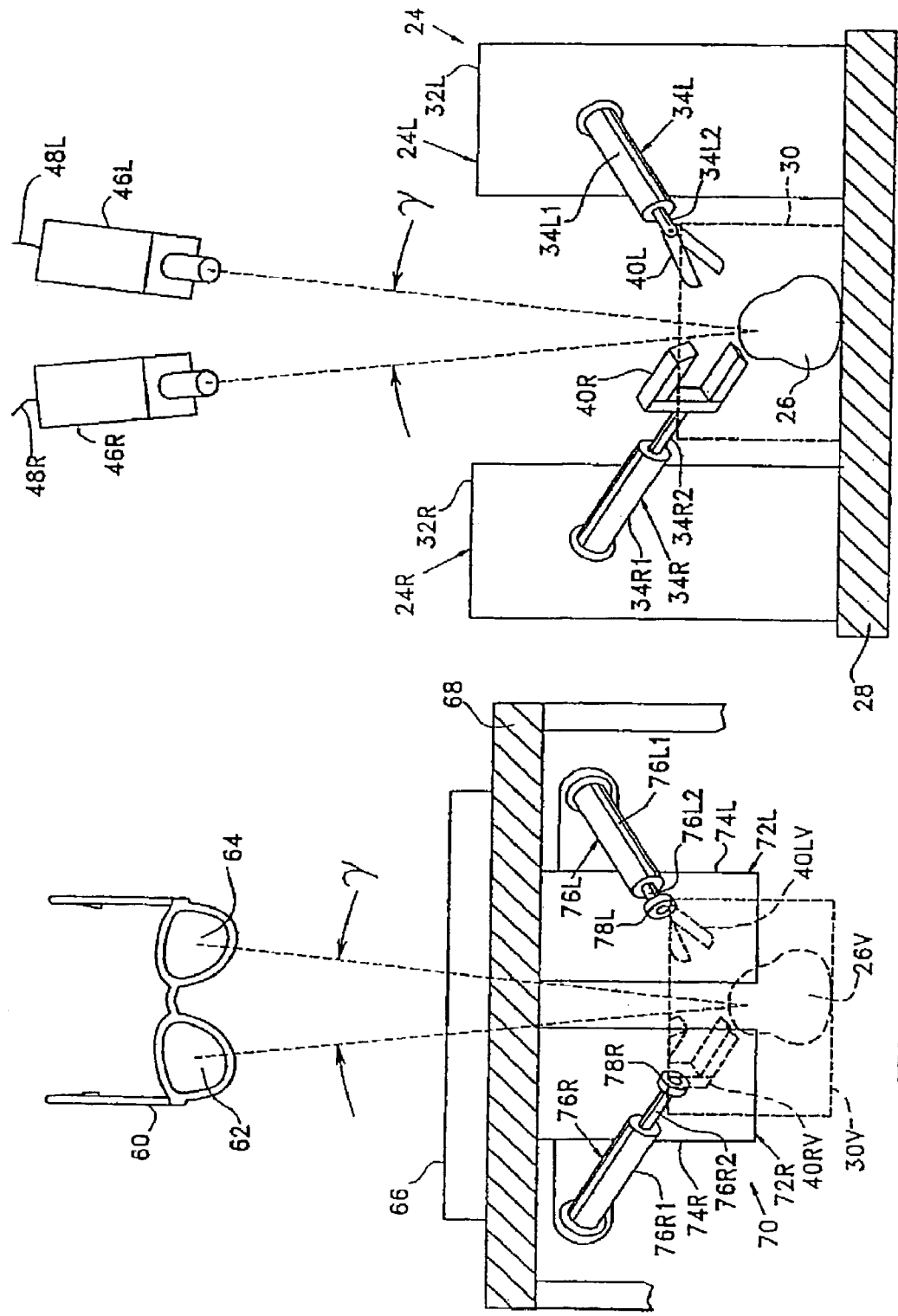

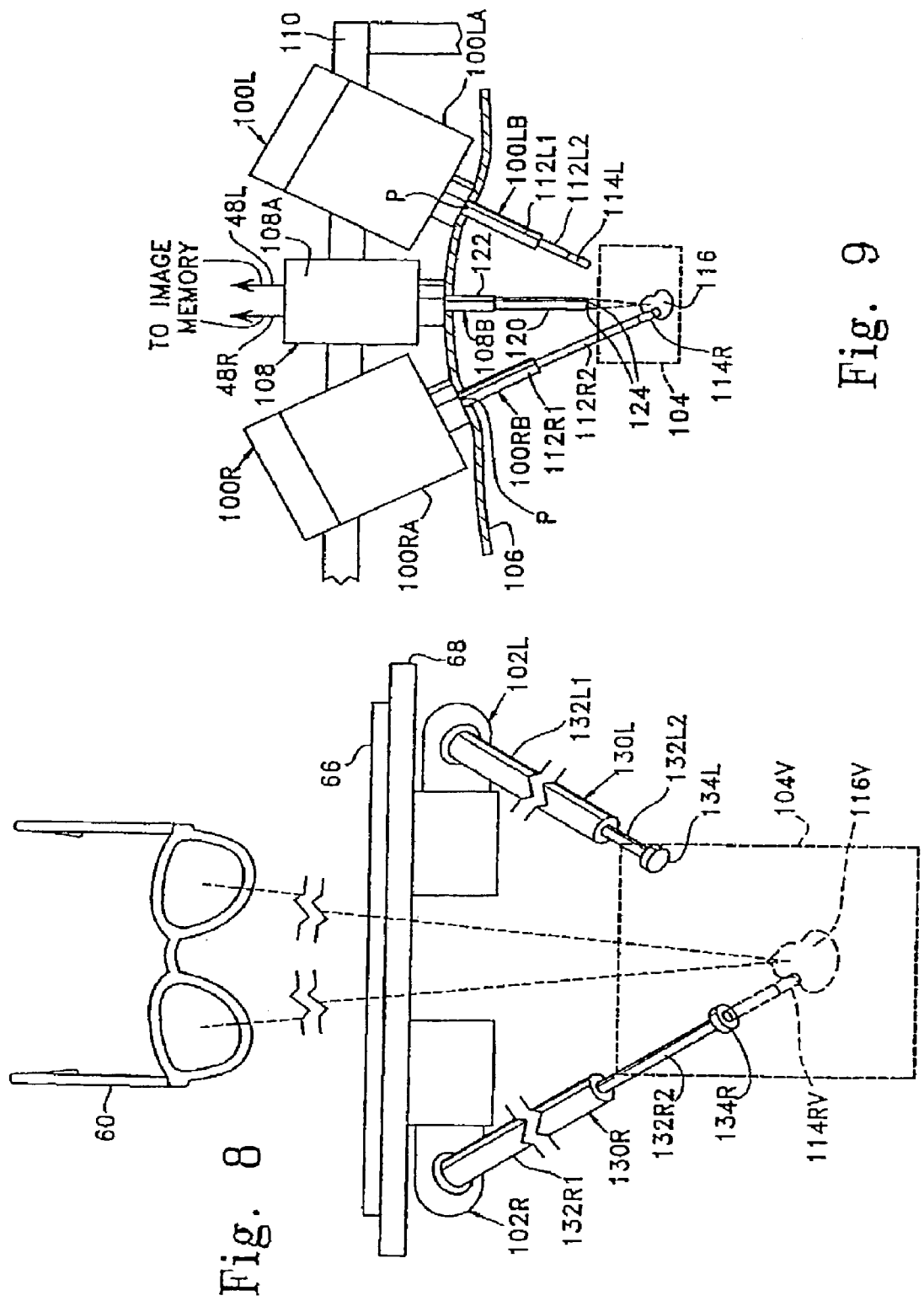

SURGICAL METHOD

This is a Continuation of application Ser. No. 07/823,932 filed Jan. 21, 1992, now abandoned.

FIELD OF THE INVENTION

This invention relates generally to teleoperator method and apparatus, and particularly to those which include means for providing the operator of remote apparatus with the same sense as working directly with his hands at the worksite.

BACKGROUND OF THE INVENTION

Teleoperating, which is well known, includes the human performance of tasks at a remote location using manipulators. Telepresense includes providing the teleoperator with the same feedback and control that he would have were he actually at the worksite carrying out the operation with his own hands. Telepresence operation generally includes use of a stationary visual display, particularly a stereographic visual display of the remote workspace. Stereoscopic television systems are well known as shown, for example, in U.S. Pat. Nos. 4,562,463 and 4,583,117 and in U.K. Patent Application GB 2,040,134.

Remote manipulators employing stereoscopic TV viewing together with force feedback also are well known as shown, for example, in an article entitled, "Controlling Remote Manipulators Through Kinesthetic Coupling," Bejczy et al, Computers in Mechanical Engineering, July 1983, pps. 48–60, and in an article entitled, "Stereo Advantage for a Peg-In-Hole Task Using a Force-Feedback Manipulator" by E. H. Spain, SPIE Vol. 1256 Stereoscopic Displays and Applications, 1990, pps. 244–254. In the Bejczy et al article, force-torque feedback is disclosed. Also, in U.S. Pat. No. 3,921,445, a manipulator which includes force, torque and slip sensors of a type which may be employed with the present invention is shown.

Even though the operator of prior art manipulators is provided with a stationary three-dimensional image of the workspace, and manual controllers for control of the manipulators are provided with feedback, the operator is not provided with a sense of actually being present at the worksite. The present invention is directed to a viewing arrangement for use in a remote manipulation system which substantially adds to the operator's sense of presence at the remote manipulator site.

SUMMARY AND OBJECT OF THE INVENTION

An object of this invention is the provision of an improved teleoperator system and method which include an improved viewing system to enhance the operator's sense of presence at remote manipulators controlled by the operator from a remote location.

An object of this invention is the provision of an improved teleoperator system and method of the above-mentioned type wherein an image of manipulator end effectors for viewing by the operator are sensed by the operator as comprising an integral part of hand-controllers used by the operator to control the end effectors, thereby giving the operator a strong sense of presence at the worksite.

An object of this invention is the provision of an improved teleoperator system and method of the above-mentioned type which is well adapted for use in a wide variety of applications including military, industrial, biomedical, and the like.

The present invention includes manipulators located at a worksite and which are controlled by hand-operated means at a remote operator control station. End effectors at the manipulators are used for manipulating objects located in a workspace at the worksite, and force-torque feedback is employed for transmitting back to the operator mechanical resistance encountered by the end effectors. Stereographic visual display means provide the operator with an image of the workspace. In accordance with the present invention, the image is located adjacent the hand-operated means so that the operator looks in the direction of the hand-operated means for viewing the image adjacent the hand-operated means. Either a real or virtual image of the workspace may be provided adjacent the hand-operated means. Display means for display of a real image may be located adjacent the hand-operated means for direct viewing of the real image by the operator. For display of a virtual image of the workspace, a mirror is located between the operator's eyes and the hand-operated means. In this case, display means provide a real image which is inverted from top to bottom, which inverted image is viewed via the mirror, which mirror inverts the image and provides the operator with a virtual image of the workspace, which appears to be located adjacent the hand-operated means. By locating the image of the workspace adjacent the hand-operated means the operator is provided with a sense that the end effectors and hand-operated means are substantially integral despite the fact the end effectors are located at the worksite and the hand-operated means are located at the remote operator's station. A stereophonic sound system may be included to provide the operator with stereophonic sound from the worksite. Video camera means are provided for viewing the workspace from which an image of the workspace is obtained. Various other sensors and associated responders may be located at the worksite and operator's station, respectively, for transmission of pressure, tactile, heat, vibration and similar information for enhanced telepresence operation.

Depending upon the application, different scaling may be provided in the transmission of information between the operator's station and worksite. For example, for microassembly, microsurgery and like operations involving small part manipulation, optical and/or video magnification may be employed to provide an enlarged 3-dimensional image for viewing by the operator. With similar scaling between the hand operated means and manipulators, the perception of the operator is substantially that which a miniature operator would have were he at the worksite.

BRIEF DESCRIPTION OF THE DRAWINGS

The invention, together with other objects and advantages thereof, will be better understood from the following description considered with the accompanying drawings. It will be understood that the drawings are for purposes of illustration and example only, and that the invention is not limited thereto. In the drawings, wherein like reference characters refer to the same parts in the several views.

FIG. 2 is an enlarged rear elevational view of the operator's station taken substantially along line 2—2 of FIG. 1;

FIG. 3 is an enlarged rear elevational view of the worksite taken substantially along line 3—3 of FIG. 1;

FIG. 8 is a rear elevational view of the operator's station shown in FIG. 7;

FIG. 9 is a rear elevational view of the worksite shown in FIG. 7;

DESCRIPTION OF THE PREFERRED EMBODIMENTS

Figure 1:
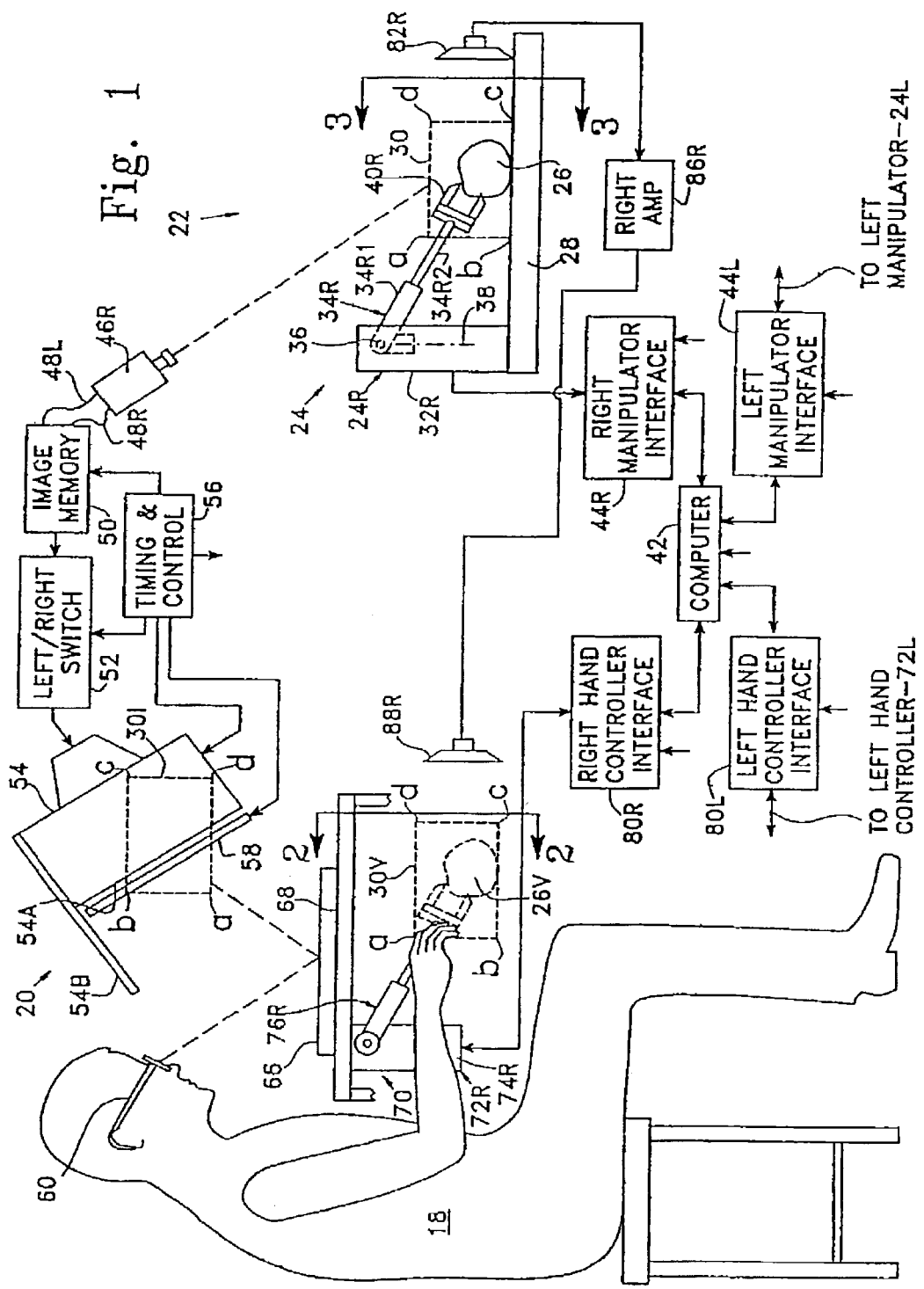
FIG. 1 is a diagrammatic showing of a teleoperator system embodying the present invention including side elevational views of a worksite and remote control operator's station.

Reference now is made to FIGS. 1–3 wherein the teleoperator system is shown to include an operator's station 20 (FIGS. 1 and 2) and worksite 22 (FIGS. 1 and 3). An operator 18 at the operator's station controls manipulator means 24 at the remote worksite. Manipulator means 24, comprising right and left manipulators 24R and 24L, respectively, are used for manipulating objects, such as object 26 which is shown located on a platform, or base, 28 within a workspace 30 shown in broken lines. For purposes of illustration only, and not by way of limitation, the right manipulator 24R is shown to comprise a housing 32R affixed to base 28 and from which housing a telescopic arm 34R extends. The inner end 34R1 of arm 34R is mounted for pivotal movement in any pivotal direction using conventional mounting means. For example, the inner end of arm 34R may be mounted for pivotal movement about a horizontal pivot axis 36 which pivot axis, in turn, is adapted for pivotal movement about vertical axis 38.

Arm 34R includes telescopic inner section 34R1 and outer section 34R2, which outer section is adapted both for axial movement into and out of inner section 34R1 and for rotation about its longitudinal axis. An end effector 40R is carried at the outer end of the arm which, for purposes of illustration, is shown to comprise a gripper. Motor means, not shown, control pivotal movement of arm 34R about pivot axes 36 and 38, axial and rotary movement of outer arm section 34R2 along and about the longitudinal axis of the arm, and opening and closing of gripper 40R. The motor means, together with motor control circuits for control of the motors, may be included in housing 32R. The motors are under control of a computer 42 connected thereto through right manipulator interface 44R and the above-mentioned motor control circuits.

The left manipulator 24L is of substantially the same design as the right manipulator 24R and the same reference numerals, but with the suffix L instead of R, are used to identify similar parts. For purposes of illustration, the left end effector 40L, shown in FIG. 3, is seen to comprise cutting blades which operate to cut in the manner of a pair of scissor blades.

The worksite is provided with a pair of video cameras 46R and 46L for viewing workspace 30 from different angles from production of stereoscopic signal outputs therefrom at lines 48R and 48L. The angle γ between the optical axes of the cameras shown in FIG. 3 is substantially equal to the operator's interocular viewing angle γ of an image of the workspace as shown in FIG. 2.

The video camera outputs at lines 48R and 48L are supplied to an image memory 50 for momentary storage of video fields of right and left images from the cameras. Fields of right and left images from image memory 50 are alternately supplied through left/right switch means 52 to visual display means 54, such as a television monitor, for alternate display of the two images at the face 54A of the monitor. Timing and control means 56 provide timing and control signals to various elements of the system, including elements included in the stereographic display system, for signal timing and control of the system. If digital storage means 50 are employed, then conversion of the camera signal outputs to digital signal form by analog to digital converter means prior to storage, and conversion of the digital signal output from left/right switch means to analog signal form in preparation for display at monitor 54 may be employed.

An electrooptical device 58 at the face of the display means 54 controls polarization of light received from display means 54 under control of a left/right synchronizing signal from timing and control unit 56. The left and right image fields are viewed by operator 18 wearing a pair of passive polarized glasses 60 having right and left polarizing elements 62 and 64 polarized in orthogonal directions. The polarization of light from display 54 through electrooptical device 58 is synchronized field by field such that the right field is occluded from the left eye and the left field is occluded from the right eye for stereographic viewing by the operator. Other means for stereographic viewing of left and right image fields are well known, including, for example, those using active stereographic glasses, which may be used in the practice of this invention to provide the operator with a stereoscopic view of the remote workspace.

The vertical deflection coil connections for monitor 54 are reversed, causing the monitor to scan from bottom to top thereby creating a top-to-bottom inverted image 30I of workspace 30. Letters a, b, c and d are used to identify corresponding corners of the workspace 30 and inverted workspace image 30I. The inverted workspace image 30I is viewed by the operator via a mirror 66 at the top of a table 68, which mirror inverts image 30I to return the image as viewed by the operator to an upright position. Looking downwardly in the direction of the mirror, the operator views a virtual image 30V of workspace 30. In accordance with one aspect of the present invention, the image viewed by the operator, which in the FIG. 1-3 embodiment comprises a virtual image, is located adjacent controller means 70 used by the operator for control of manipulator means 24 at the worksite.

Controller means 70 are shown located beneath the table top 68 and include right and left controllers 72R and 72L for control of the respective right and left manipulators 24R and 24L. The right and left controllers are of substantially the same design so that a description of one applies to both. As with the manipulators, the suffixes R and L are used to distinguish elements of the right controller from those of the left controller. For purposes of illustration, and not by way of limitation, the right controller 72R is shown to comprise a housing 74R affixed to the bottom of table top 68 and from which hand-operated means 76R in the form of a telescopic control arm, or stick, extends.

The right and left control arms 76R and 76L are provided with the same degrees of freedom as the associated manipulator arms 34R and 34L, respectively. For example, the inner end of control arm 76R is mounted for pivotal movement about a horizontal pivot axis, corresponding to manipulator pivot axis 36, which axis, in turn, is adapted for pivotal movement about an intersecting vertical axis, corresponding to manipulator axis 38. Control arm 76R also includes inner section 76R1 and outer section 76R2, which outer section is adapted both for axial movement into and out of inner section 76R1 and for rotation about its longitudinal axis. It will be apparent that the control arm 76R is provided with the same four degrees of freedom as the associated manipulator arm 34R. Additionally, sensor means 78R are located adjacent the outer end of outer arm section 76R2 for use in controlling gripping action of gripper 40R. Similar sensor means 78L adjacent the outer end of control arm 76L are adapted for use in controlling operation of scissor blades 40L.

Right and left controllers 72R and 72l are included in a servomechanism system wherein mechanical motion of control arms 76R and 76L controls the position of manipulator arms 34R and 34L, and pressure on sensor means 78R and 78L controls opening and closing of end effectors 40R and 40L, respectively. In FIG. 1, right and left hand controller interfaces 80R and 80L, respectively, are shown for connection of the controllers to computer 42. Servomechanisms for control of mechanical motion at a remote location are well known, including those which provide force and torque feedback from the manipulator to the hand-operated controller means. Any suitable prior art servomechanism may be used in the practice of the present invention, with those incorporating force and torque feedback being particularly preferred for telepresence operation of the system. In the illustrated system, right and left microphones are included at the worksite, outputs from which microphones are amplified by right and left amplifiers and supplied to right and left speakers at the operators' station for providing a stereophonic sound output to provide the operator with an audio perspective present at the workspace. In FIG. 1, only the right channel of the stereophonic system is shown including right microphone 82R, right amplifier 86R and right speaker 88R. The left microphone and speaker are located directly behind the respective right microphone and speaker at the worksite and operator's control station as viewed in FIG. 1. Obviously, earphones may be provided for use by the operator in place of the speakers which would help to block out external noises at the operator's control station. Also, in FIG. 1 a light shield 54B at the monitor is shown for blocking direct viewing of the monitor face by the operator.

Figure 4:
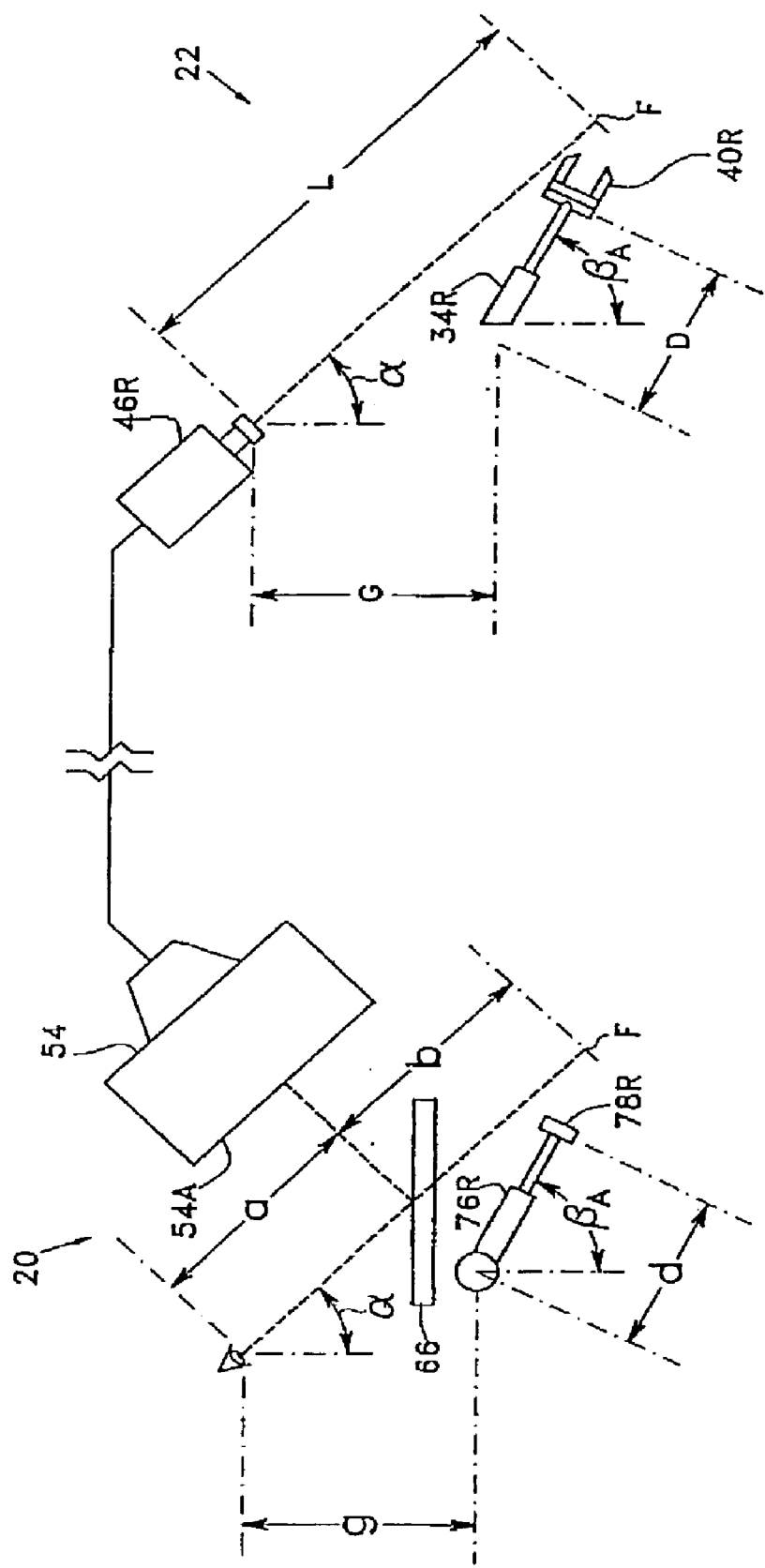
FIG. 4 is a simplified side elevational view which is similar to FIG. 1 and showing dimensional relationships between elements at the worksite and elements at the operator's station.

Reference now is made to FIG. 4 wherein a simplified diagrammatic view of the system illustrated in FIGS. 1–3 is shown and wherein various lengths and angular positions are identified by reference characters. In FIG. 4, the optical path length between the cameras and a point F at the workspace is identified by reference character L. A corresponding path length between the operator's eyes and point F at the virtual image of the workspace is identified by the distance a+b, where a is the distance from the eyes of the operator to mirror 66, and b is the distance from the mirror to point F at the virtual image. Other dimensions shown include the height G of the cameras above the pivot point of manipulator arm 34R and corresponding height g of the operator's eyes above the pivot point of control arm 76R. With the control arm 76R at length d, the manipulator arm 34R adjusts to length D. Similarly, with the control arm 76R at an angle $\beta_A$ with the vertical, the manipulator arm 34R is positioned at the same angle from vertical. The angle from vertical at which the cameras view the workspace and the eyes view the virtual image of the workspace is identified by $\alpha$.

Between elements of the worksite and operator station, the following relationships pertain:

$$a+b=kL, \qquad (1)$$

$$d=kD, \text{ and} \qquad (2)$$

$$g=kG \qquad (3)$$

where k is a scale factor constant.

When k equals 1 such that a+b=L, d=D and g=G, no scaling of worksite dimensions is required.

Any scale factor may be employed, the invention not being limited to full-scale manipulation. For example, the worksite can be small, including microscopic in size, in which case the optical parameters, including distance to object, interocular distance and focal length, and mechanical and dimensional paramaters are appropriately scaled.

By using appropriate scaling and image magnification and force and torque feedback, and by locating the image 30V of the workspace 30 adjacent hand-operated control means 76R and 76L, the operator is provided with a strong sense of directly controlling the end effectors 40R and 40L. The operator is provided with a sense that the end effectors 40R and 40L and respective control arms 76R and 76L are substantially integral. This same sense of togetherness of the hand-operated control means and end effectors is not provided in prior art arrangements wherein the image viewed by the operator is not located adjacent the hand-operated control means. Even where the prior art includes stereoscopic viewing and force and torque feedback, there is a feeling of disconnectedness of the hand motions from the visual image object being worked upon. The present invention overcomes this sense of disconnectedness by locating the workspace image where the operator's hands appear to exercise direct control over the end effectors.

Figure 5:
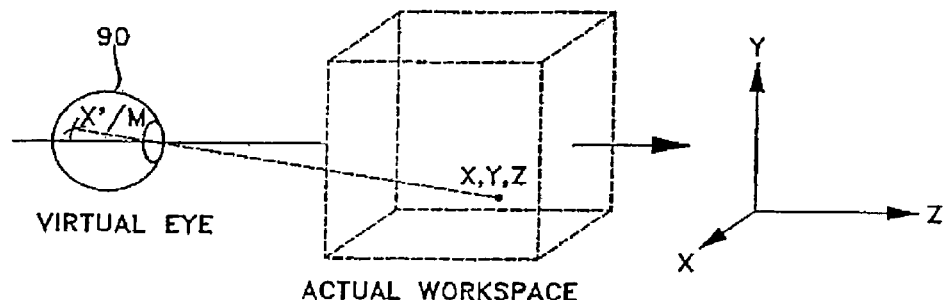
FIG. 5 is a diagrammatic view to illustrate visual perception by a miniature virtual eye.
Figure 6:
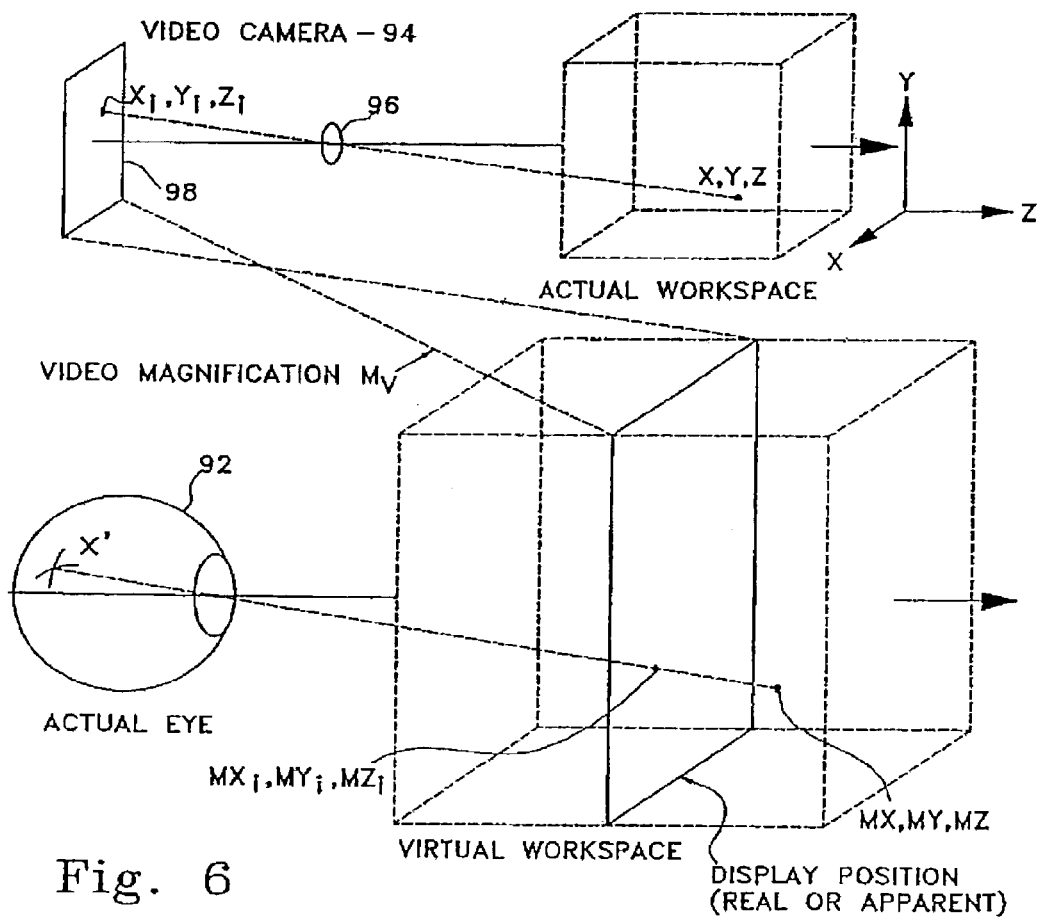
FIG. 6 is a diagrammatic view to illustrate visual perception by the operator when image magnification is employed.

For small-scale manipulation, such as required for surgical applications, it is desired to replicate the visual experience that a miniature observer would have were he closely adjacent the actual worksite. In FIG. 5, the virtual eye 90 of a hypothetical miniature observer is shown viewing an actual workspace. Light from a source at a point X, Y, Z in the actual workspace produces a stimulus on the miniature observer's eye 90 at a point identified as X'/M. In FIG. 6, an eye 92 of an actual operator is shown viewing an enlarged image of the virtual workspace produced by means of a video camera 94 used to view the actual workspace. The illustrated camera includes a light-receiving lens 96 and solid state imaging device such as a charge-coupled-device (CCD) array 98 where the point light source at X, Y, Z is shown imaged at point $X_i$, $Y_i$, $Z_i$. With correct scaling, a corresponding light source is produced at point $MX_i$, $MY_i$, $MZ_i$ at either the real or apparent position of the face of the visual display which, due to stereoscopic operation of the system appears to the operator to originate from point MX, MY, MZ corresponding to point X,Y,Z at the actual workspace. At the retina of the actual eye 92, a stimulus is produced at point X' at proportionately the same position as point X'/M at eye 90 of the hypothetical observer. This relationship is ensured by selecting a correctly scaled camera distance and lens focal length such that the optical magnification $M_o=M/M_v$ where M is the desired overall magnification and $M_v$ is the video magnification. A typical video magnification, $M_v$, which equal the ratio of the CCD-array 98 width to the display width, is about 40.

Figure 7:
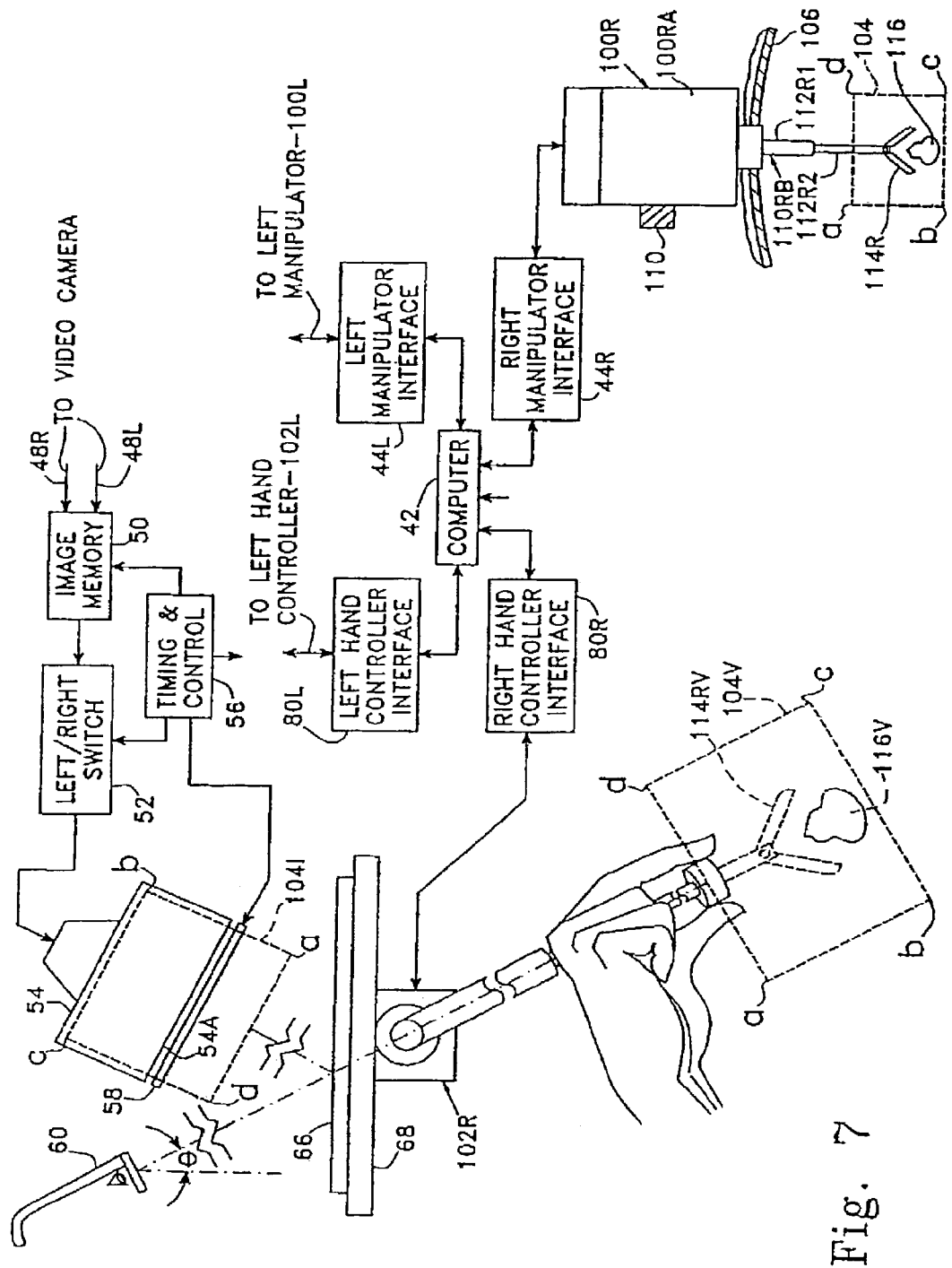
FIG. 7 is a diagrammatic view which is similar to that of FIG. 1 but showing the teleoperator system used for telepresence surgery.

Reference now is made to FIGS. 7 through 9 wherein a modified form of this invention is shown for medical use. Here, right and left manipulators 100R and 100L are shown which are under control of right and left controllers 102R and 102L, respectively. Elements of the imaging system are substantially the same as those employed in the imaging system illustrated in FIGS. 1–3 described above except that an enlarged virtual image 104V of actual workspace 104 is provided for viewing by the operator. Also, servomechanism elements for connection of the right and left controllers 102R and 102L to the respective manipulators 100R and 100L are substantially the same as those described above with reference to FIGS. 1–3. In the illustrated arrangement, the right and left manipulators are of substantially the same construction as are the right and left controllers, such that a description of one manipulator and one controller applied to both. Again, suffixes R and L are used to distinguish between right and left elements thereof.

The manipulators include outer control sections 100RA and 100LA end insertion sections 100RB and 100LB, which insertion sections are adapted for insertion into a body cavity through cylindrical tubes, or cannulas, not shown. For purposes of illustration, the manipulators are shown inserted through the abdomen wall 106 of a subject. As is well understood, for laparoscopic surgical procedures, wall 106 is separated from internal organs by insufflation wherein a gas is introduced into the abdomen by any suitable means not shown. Manipulator motors and associated motor control circuits are contained in the outer control sections 100RA and 100LA of the manipulators for control of the insertion section. The manipulators, together with a laparoscope 108 for viewing organs within the cavity, are carried by a fixed rail 110 forming part of a surgical table upon which the subject is supported.

The insertion sections 100RB and 100LB of the manipulators may be of substantially the same design as manipulator arms 34R and 34L described above with reference to the FIGS. 1–3 embodiment. The insertion sections are of relatively small size for use inside the body. Insertion section 100RB includes telescopic inner section 112R1 and outer section 112R2, which outer section is adapted for both axial movement into and out of inner section 112R1 and for rotation about its longitudinal axis. End effectors 114R and 114L are carried at the outer ends of the respective right and left sections 112R2 and 112L2 for manipulation of organ 116. The inner section 112R1 is adapted for pivotal movement about intersecting perpendicular axes located substantially at point P where the insertion section intersects wall 106. Exclusive of operation of end effectors 114R and 114L the manipulator arms each are provided with four degrees of freedom, the same as in the embodiment shown in FIGS. 1–3. End effectors 114R and 114L simply may comprise, essentially, microsurgical instruments with their handles removed including, for example, retractors, electrosurgical cutters and coagulators, microforceps, microneedle holders, dissecting scissors, blades, irrigators, and sutures.

Laparoscope 108 for viewing the workspace 104 is shown comprising an outer operating section 108A and insertion section 108B. The outer end section 120 of insertion section 108B is axially and rotatably movable within the inner end 122 thereof, and is provided with a pair of image transmission windows 124,124 for stereoscopic viewing of workspace 104. The laparoscope also is provided with illuminating means, not shown for illuminating the workspace, and with liquid inlet and outlet means, not shown, for flow of liquid past the windows. Video camera means within section 108A are responsive to light received through the viewing windows for generation of left and right electronic images at output lines 48R and 48L for connection to image memory 50. A magnified 3-dimensional image 104I is produced at display means 54 for viewing by the operation wearing cross-polarized glasses 60 via mirror 66. As with the embodiment shown in FIGS. 1–3, a virtual image 104V of the workspace 104 is produced adjacent control arms 130R and 130L of controllers 102R and 102L. Control arms 130R and 130L are of the same type as control arms 76R and 76L included in the FIGS. 1–3 embodiment described above. They include telescopic inner and outer sections 132R1 and 132R, and 132L1 and 132L2. Sensor means 134R and 134L located adjacent the outer ends of the control arms control operation of end effectors 114R and 114L, respectively, in the manner described above with reference to FIGS. 1–3. It here will be noted that the angle from vertical at which the image is viewed by the operator need not equal the angle from vertical at which the object is viewed by the cameras. In the arrangement illustrated in FIGS. 7–9, the operator is shown to view the image 104V at an angle θ from vertical (FIG. 7) whereas the object 116 is shown as viewed directly downwardly. With no external reference, the sense of vertical within a body is not particularly great, and no confusion is produced in the mind of the operator as a result of the different observer and camera viewing angles relative to vertical.

With the FIGS. 7–9 embodiment, not only is a magnified virtual image 104V of the workspace provided for viewing by the operator, but control arms 130R and 130L of greater length than the length of the manipulator insertion sections 100RB and 100LB are employed. Servomechanism scaling of axial movement of the telescopic control arms is provided such that axial extension or retraction thereof results in a smaller extension or retraction of the telescopic insertion sections. Angular pivotal motion of the control arms 130R and 130L produces the same angular pivotal motion of insertion sections 100RB and 100LB, and rotational movement of the end sections 132R2 and 132L2 of the control arms produces the same rotational motion of end sections 112R2 and 112L2 of the insertion sections of the right and left manipulators, without scaling. This embodiment of the invention, with its magnified image, is of particular use in the area of microsurgery, and especially in those cases where the surgeon cannot reach an area by hand because of size constraints.

Figure 11:
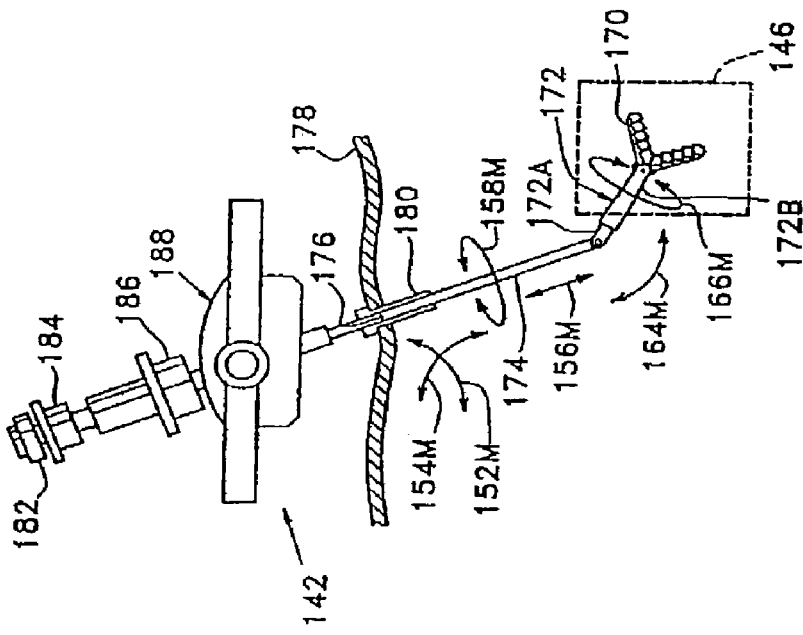
FIGS. 10 and 11 are fragmentary side elevational views of modified forms of operator's station and manipulator, respectively, having increased degrees of freedom.
Figure 10:
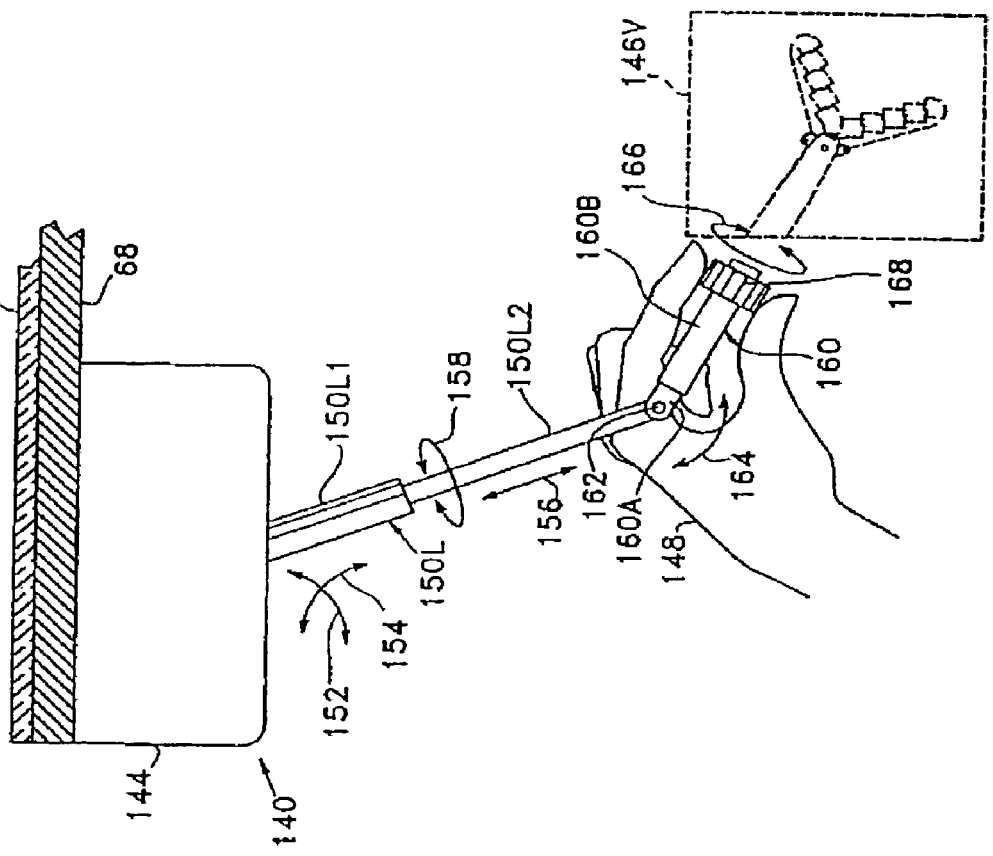

The present invention is not limited to use with manipulators having any particular number of degrees of freedom. Manipulators with different degrees of freedom which are well known in the art may be used in the practice of this invention. In FIGS. 10 and 11, to which reference now is made a controller 140 and manipulator 142, respectively, are shown which include a wrist joint to provide the same with additional freedom of movement. The illustrated controller 140 includes a housing 144 affixed to the bottom of table top 68 upon which table mirror 66 is located. An enlarged virtual image 146V of actual workspace 146 is provided adjacent the operator's hand 148 viewable by the operator when looking downwardly onto the mirror 66 in a manner described above.

A control arm 150L comprising inner and outer sections 150L1 and 150L2, respectively, is mounted within housing 144 for pivotal movement in any pivotal direction as indicated by intersecting double-headed arrows 152 and 154.

The outer section 150L2 is adapted for axial movement into and out of inner section 150L1 in the direction of double-headed arrow 156. It also is adapted for rotation about its longitudinal axis in the direction of double-headed arrow 158. In this embodiment, the control arm includes an end section 160 pivotally attached to outer section 150L2 by wrist joint 162 for pivotal movement in the direction of double-headed arrow 164. End section 160 comprises axially aligned inner and outer sections 160A and 160B, the outer section 160B of which is rotatable about its longitudinal axis in the direction of double-headed arrow 166. As with the above-described arrangements, sensor means 168 are located adjacent the free end of the control arm for operation of an end effector 170 at manipulator 142 shown in FIG. 11.

Referring to FIG. 11, end effector 170 is shown to comprise a pair of movable jaws attached to a wrist 172 comprising axially aligned links 172A and 172B. Outer link 172B is rotatable about its longitudinal axis relative to inner link 172A by motor means, not shown, in the direction of double-headed arrow 166M in response to rotation of section 160B of the hand-operated control unit in the direction of arrow 166. Wrist link 172A is pivotally attached to a shaft or manipulator forearm 174 for pivotal movement in the direction of double-headed arrow 164M in response to pivotal movement of end section 160 of the hand-operated control means about pivot axis 162. Forearm 174 is longitudinally axially movable in the direction of double-headed arrow 156M in response to axial movement of outer section 150L2 of control arm 150L in the direction of double-headed arrow 156. It also is rotatable about its longitudinal axis in the direction of double-headed arrow 156M in response to rotation of outer section 150L2 of control arm 150L in the direction of double-headed arrow 158. Additionally, it is pivotally movable about point 176 in the directions of double-headed arrows 152M and 154M in response to pivotal movement of control arm 150L in the directions of double-headed arrows 152 and 154, respectively. For biomedical use, such as remote laparoscopic surgery, pivot point 176 is substantially located at the level of abdominal wall 178 through which the manipulator extends. In FIG. 11, manipulator arm 174 is shown extending through a cannula 180 which penetrates the abdominal wall.

The outer operating end of the manipulator is adapted for attachment to a supporting rail, not shown, of the surgery table upon which the subject is supported. It includes an end effector drive motor 182 for opening and closing of gripper 170. Wrist drive motor 184 controls pivotal movement of wrist 172 in the direction of double-headed arrow 164M, and extension drive motor 186 controls axial movement of manipulator arm 174 in the direction of double-headed arrow 156M. Forearm pivotal control motors and linkages, identified generally by reference numeral 188, provide for pivotal movement of arm 174 about pivot point 176 in the directions of arrows 152M and 154M. Pivotal motion about point 176 is provided by simultaneous lateral movement of the outer operating end of the manipulator and pivotal movement of arm 174. Movements are coordinated such that the center of rotation of forearm 174 is fixed in space at point 176 at the level of the abdominal wall.

Controller 140 and manipulator 142 are included in a system such as shown in FIGS. 7, 8 and 9 which includes a second controller and manipulator for use by the operator's right hand, and associated servomechanism means of any suitable type, not shown, for remote control of the manipulators by the hand-operated controllers. Video camera means at the worksite, such as shown in FIG. 9, together with display means, such as shown in FIG. 7, are employed for providing the operator with an image of the workspace at a location adjacent the left and right hand-operated control means. By using manipulators with a wrist joint, an added degree of freedom is provided for increased maneuverability and usefulness thereof. However, as noted above, the present invention is not limited to use with manipulators with any particular degree of freedom.

Figure 13:
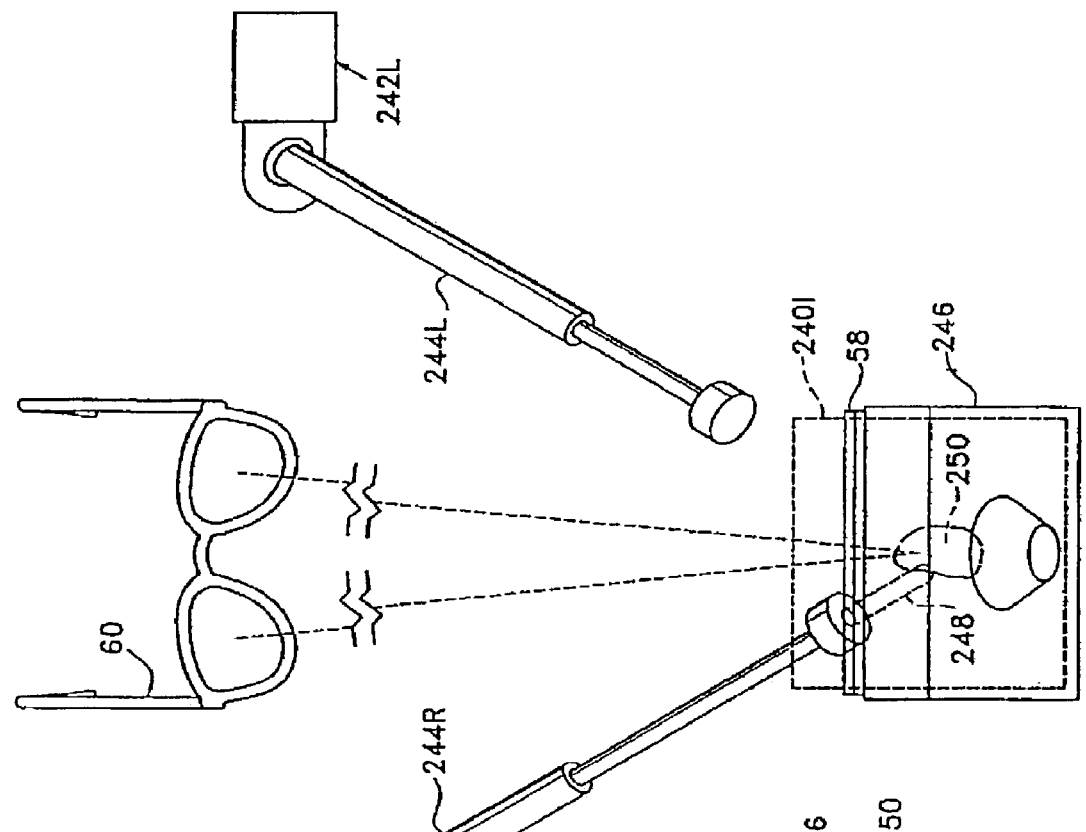
FIG. 13 is a rear elevational view of the modified form of operator's station shown in FIG. 12.
Figure 12:
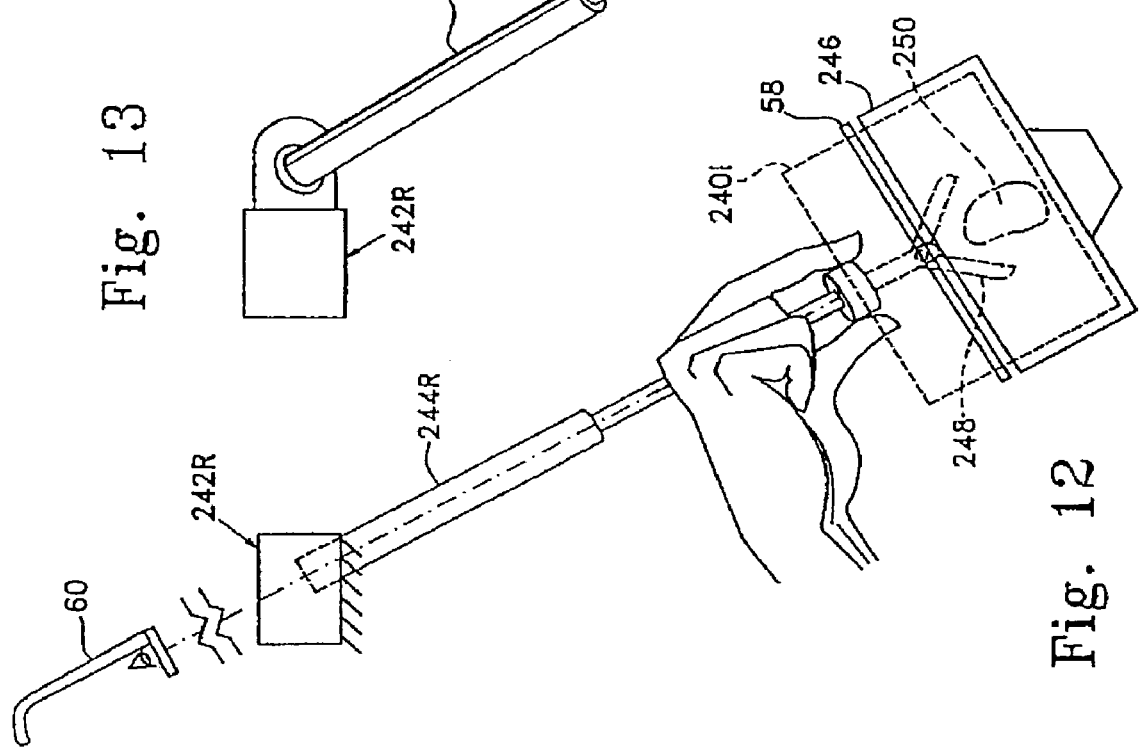
FIG. 12 is a side elevational view of a modified form of operator's station wherein display means are positioned for direct viewing by the operator.

Reference now is made to FIGS. 12 and 13 wherein a modified form of this invention is shown which provides for direct viewing of a 3-dimensional image 240I of a workspace, not shown. In FIGS. 12 and 13, only the operator's station is shown, which includes right and left controllers 242R and 242L and associated right and left hand-operated means 244R and 244l which may be of the same type as controllers and control arms described above. The operator's station is adapted for remote control of manipulators which also may be of the above-described type. The 3-dimensional image 240I of the workspace is provided by visual display means 246 in conjunction with electrooptical device 58 at the face of the display means and cross-polarized glasses 60 worn by the operator, to which display means left and right video fields from left and right video cameras that view the workspace are alternately supplied, all in the manner described in detail above. End effector and object images 248 and 250, respectively, are shown within the workspace image as viewed by video cameras at the worksite. The display means 246 is located adjacent the left and right hand-operated means 244R and 244L for direct viewing by the operator. With this arrangement, the end effector and object images together with the hand-operated means 244R and 244L are simultaneously viewable by the operator. Since the hand-operated means also are visible, the operator is provided with a visual sense of connection between the end effector means and hand-operated means whereby they appear substantially as being integral.

Figure 14:
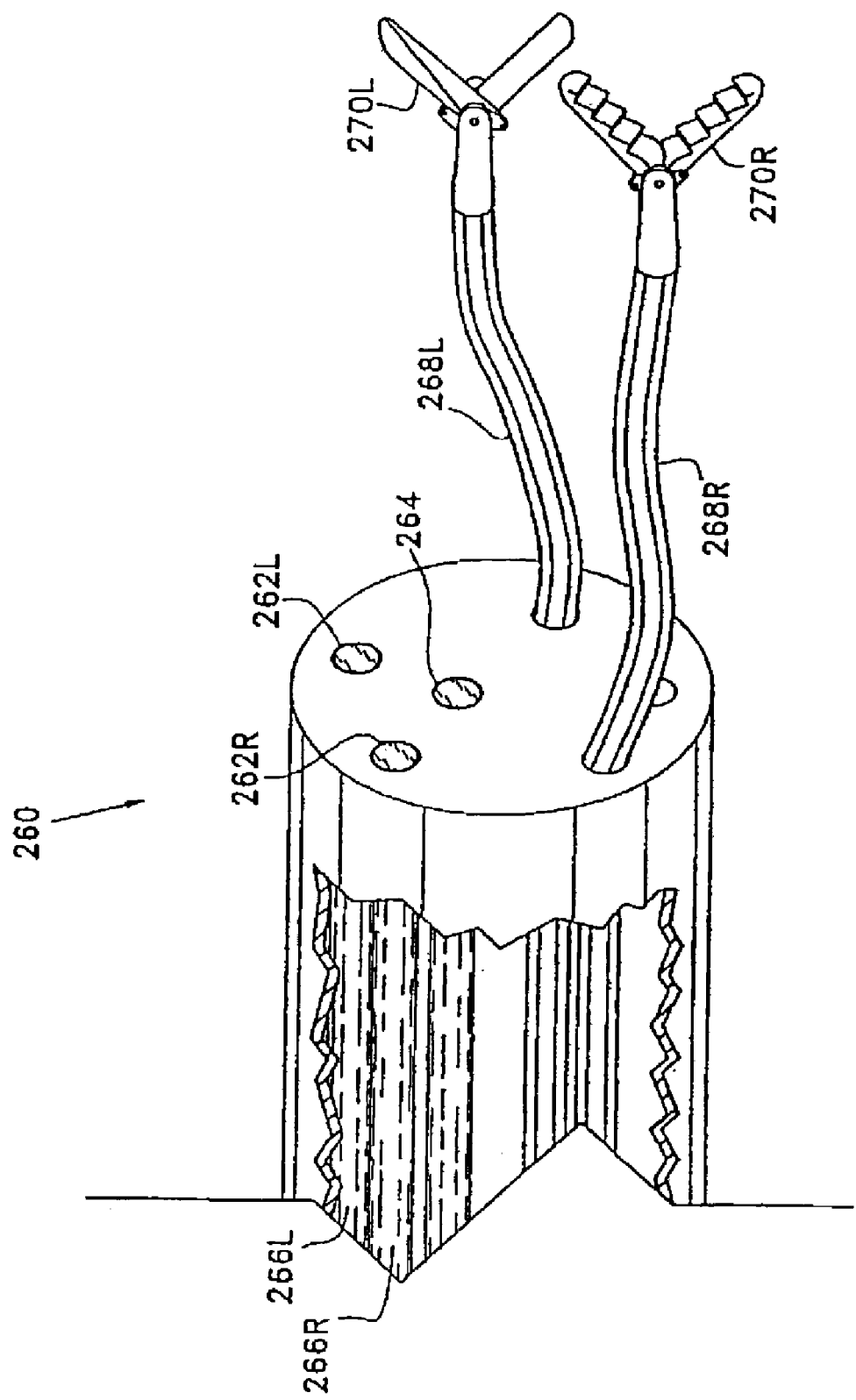
FIG. 14 shows a fragmentary portion of the insertion portion of an endoscope for use with the present invention.

Reference now is made to FIG. 14 wherein the distal end portion, or tip, 260 of the insertion section of an endoscope is shown which is of substantially the same type as shown in the above-mentioned publication entitled "Introduction to a New Project for National Research and Development Program (Large-Scale Project) in TY 1991" which endoscope may be used in the practice of the present invention. The insertion end of the endoscope includes a pair of spaced viewing windows 262R and 262L and an illumination source 264 for viewing and illuminating workspace to be observed. Light received at the windows is focused by objective lens means, not shown, and transmitted through fiber-optic bundles to a pair of cameras at the operating end of the endoscope, not shown. The camera outputs are converted to a 3-dimensional image of the workspace which image is located adjacent hand-operated means at the operator's station, not shown. Right and left steerable catheters 268R and 268L pass through accessory channels in the endoscope body, which catheters are adapted for extension from the distal end portion, as illustrated. End effectors 270R and 270L are provided at the ends of the catheters which may comprise conventional endoscopic instruments. Force sensors, not shown, also are inserted through the endoscope channels. Steerable catheters which include control wires for controlling bending of the catheters and operation of an end effector suitable for use with this invention are well known. Control motors for operation of the control wires are provided at the operating end of the endoscope, which motors are included in a servomechanism of a type described above for operation of the steerable catheters and associated end effectors from a remote operator's station. As with the other embodiments, the interfacing computer in the servomechanism system remaps the operator's hand motion into the coordinate system of the end effectors, and images of the end effectors are viewable adjacent the hand-operated controllers in a manner described above. With this embodiment, the operator has the sensation of reaching through the endoscope to put his hands directly on the end effectors for control thereof. Endoscopes of different types may be employed in this embodiment of the invention so long as they include one or more accessory channels for use in control of end effector means, and suitable viewing means for use in providing a visual display of the workspace. For example, gastric, colonscopic, and like type, endoscopes may be employed.

The invention having been described in detail in accordance with requirements of the Patent Statutes, various other changes and modifications will suggest themselves to those skilled in this art. For example, as noted above, the invention may include the use of tactile feedback to provide the subtle sensations for palpation and for manipulating tissues and instruments. To provide this feedback, tactile sensor arrays may be included on the end effectors which are coupled to tactile sensor stimulator arrays on the hand-operated control means, which reproduce the tactile sensation on the operator's hands. A variety of transduction technologies for teleoperator tactile sensing are known including resistive/conductive, semiconductor, piezoelectric capacitive and photoelectric. Hand-operated control means and manipulators of different types may be employed using a wide variety of well-known mechanisms and electromechanical elements including, for example, gimbals, linkages, pulleys, cables, drive belts and bands, gears, optical or electromagnetic position encoders, and angular and linear motors. Force feedback to the operator requires use of body contact with hand-operated control means. Both hand grip type hand controllers such as those illustrated, and control brace type hand controllers are well adapted for use with the present invention for force feedback to the operator. Control brace hand controllers include use of structures with positive sensors mounted on the operator at joints for measuring joint angles. Force feedback then can be applied to each joint. Similarly, light fabric gloves with variable-resistance or fiber-optic flex sensors mounted on the joints for measuring bending of individual fingers may be used. Gloves of this type also may be provided with force feedback to provide for telepresence interaction with real objects. Regardless of the type of hand-operated control means employed, an image of the workspace is produced adjacent thereto to provide the operator with a sense that the end effector means and hand-operated control means are substantially integral. Also, as noted above, servomechanisms of many different types are well known in the robotic and teleoperator system arts, and the invention is not limited to any particular type. Those that include force and torque feedback to the operator are preferred to contribute to a telepresence sense of operation. In addition, many different means for producing a stereoscopic image of the workspace are known. For example, instead of using two cameras, a single camera may be employed together with switched cross-polarizing elements in the image receiving path. In this case, a pair of spaced stereoscopic lenses are used for viewing the workspace from different angles and providing first and second images thereof to the camera. In the FIG. 9 arrangement, wherein a laparoscope is shown, other types of endoscopes may be used for viewing the workspace. As noted above, the invention is not limited to any particular application or use. In the biomedical field, uses include, for example, open surgery, including surgery from a remote location, microsurgery, and minimum invasive surgery such as laparoscopic and endoscopic surgery. Laboratory use including microscopic manipulation also is contemplated. Industrial use of the invention include, for example, hazardous materials handling, remote operations, microassembly, and the like. Military and undersea use of the teleoperator system of this system are apparent. It is intended that the above and other such changes and modifications shall fall within the spirit and scope of the invention defined in the appended claims.

I claim:

1. A method for allowing a user to remotely control a movement of a surgical instrument having a tip, the method comprising the steps:
    a) establishing an original position of the surgical instrument tip;
    b) inputting a command provided by a user to move the surgical instrument in a desired direction relative to an object displayed on a display device;
    c) computing an incremental movement of the surgical instrument based on the command provided by the user and on the original position of the surgical instrument;
    d) moving the surgical instrument in the desired direction so that the surgical instrument tip always moves in a direction commanded by the user.

2. The method of claim 1, further comprising:
    1) providing a first articulate arm, a controller and an input device which receives input commands, the first articulate arm in electrical communication with the controller and the controller in electrical communication with the input device;
    2) cutting at least one incision into a patient;
    3) attaching the surgical instrument to the first articulate arm, the surgical instrument having a shaft supporting the surgical instrument tip;
    4) inserting said surgical instrument into the patient through the at least one incision such that a first portion of the shaft is outside the patient and a second portion of the shaft is inside the patient;
    5) generating movement commands to move said surgical instrument in accordance with a surgical procedure being performed, wherein said first articulate arm moves said surgical instrument in accordance with the movement commands such that said first portion of the shaft and said second portion of the shaft move; and
    6) removing the surgical instrument from the patient.

3. The method of claim 2 wherein said surgical instrument is a grasper.

4. The method of claim 2 wherein the surgical instrument is a cauterizer.

5. The method of claim 2 wherein the surgical instrument is a cutting blade.

6. The method of claim 2, further comprising:
    inputting the commands by moving a handle, the handle supported by an input linkage and having a sensor, wherein the surgical instrument comprises an articulable surgical instrument having a wrist joint coupling the shaft to the surgical instrument tip, wherein said first articulate arm moves said surgical instrument while the first portion of the shaft is outside the patient and the second portion of the shaft is inside the patient by rotating the shaft about an axis of the shaft, by translating the shaft along the axis of the shaft, and by articulating the wrist joint within the patient, the surgical instrument movement proportional with the handle movement; and operating a joint coupling a first tip structure and a second tip structure of the surgical instrument by actuating the sensor of the handle.

7. A medical robotic system, comprising:
a robotic arm;
a coupler that pivotally attaches to the arm;
an endoscopic surgical instrument that is held by said coupler; and
a controller having a handle, the controller in electrical communication with the robotic arm; and
wherein movement at the controller produces a proportional movement of the robotic arm and surgical instrument, and wherein said endoscopic surgical instrument is an articulable endoscopic surgical instrument; and
wherein the articulable surgical instrument comprises a shaft coupled to a surgical instrument tip by a wrist joint, the articulable surgical instrument insertable into a patient via an incision such that a first portion of the shaft is outside the patient and a second portion of the shaft is inside the patient; wherein the handle has a sensor and is supported by a linkage, wherein movement of the handle produces rotation of said first portion of the shaft and the second portion of the shaft about an axis of the shaft extending through the incision, translation of said shaft along the axis, and articulation of said wrist joint, and wherein actuation of the sensor of the handle produces operation of the surgical instrument tip.

8. A system that allows a user to control a movement of a surgical instrument, wherein the surgical instrument is coupled to a display device that displays an object, comprising:
a mechanism that moves the surgical instrument, said mechanism having an original position and including a first linkage arm coupled to the surgical instrument and a first actuator which can rotate said first linkage arm and the surgical instrument in a plane perpendicular to a first axis, said first actuator being coupled to a linear actuator which can translate said first linkage arm along an axis parallel with the first axis;

an input device that receives a command to move the surgical instrument in a desired direction relative to the object displayed by the display device, the input device having a handle; and,
a controller that receives said command to move the surgical instrument in the desired direction, computes a movement of said mechanism based on said command and the original position of said mechanism so that the surgical instrument moves in the desired direction, and provides output signals to said mechanism to move said mechanism said computed movement to move the surgical instrument in the desired direction commanded by the suer, movement at the input device producing a proportional movement of the surgical instrument.

9. A system that allows a user to control a movement of a surgical instrument, wherein the surgical instrument is coupled to a display device that displays an object, comprising:
a mechanism that moves the surgical instrument, said mechanism having an original position and including a first linkage arm coupled to the surgical instrument and a first actuator which can rotate said first linkage arm and the surgical instrument in a plane perpendicular to a first axis, said first actuator being coupled to a linear actuator which can translate said first linkage arm along an axis parallel with the first axis;
an input device that receives a command to move the surgical instrument in a desired direction relative to the object displayed by the display device; and,
a controller that receives said command to move the surgical instrument in the desired direction, computes a movement of said mechanism based on said command and the original position of said mechanism so that the surgical instrument moves in the desired direction, and provides output signals to said mechanism to move said mechanism said computed movement to move the surgical instrument in the desired direction commanded by the user; wherein said controller comprises a computer which receives input signals from said input device and provides output signals to move the surgical instrument.

* * * * *